US010080745B2

(12) United States Patent
Stone et al.

(10) Patent No.: US 10,080,745 B2
(45) Date of Patent: Sep. 25, 2018

(54) PIERICIDIN BACTERIAL INHIBITORS

(71) Applicant: The Regents of the University of California Santa Cruz, Oakland, CA (US)

(72) Inventors: Victoria Auerbuch Stone, Santa Cruz, CA (US); Roger G. Linington, Felton, CA (US); Weng Ruh Wong, Santa Cruz, CA (US); Miles C. Duncan, Santa Cruz, CA (US)

(73) Assignee: The Regents of the University of California Santa Cruz, Oakland, CA (US)

( * ) Notice: Subject to any disclaimer, the term of this patent is extended or adjusted under 35 U.S.C. 154(b) by 0 days.

(21) Appl. No.: 15/039,116

(22) PCT Filed: Nov. 24, 2014

(86) PCT No.: PCT/US2014/067006

§ 371 (c)(1),
(2) Date: May 25, 2016

(87) PCT Pub. No.: WO2015/077672

PCT Pub. Date: May 28, 2015

(65) Prior Publication Data

US 2017/0157099 A1 Jun. 8, 2017

Related U.S. Application Data

(60) Provisional application No. 61/908,405, filed on Nov. 25, 2013.

(51) Int. Cl.

| | |
|---|---|
| ***A61K 31/44*** | (2006.01) |
| ***G01N 33/94*** | (2006.01) |
| ***G01N 33/50*** | (2006.01) |

(52) U.S. Cl.
CPC ......... *A61K 31/44* (2013.01); *G01N 33/5008* (2013.01); *G01N 33/94* (2013.01); *G01N 2333/24* (2013.01); *G01N 2333/986* (2013.01); *G01N 2560/00* (2013.01)

(58) Field of Classification Search
None
See application file for complete search history.

(56) References Cited

U.S. PATENT DOCUMENTS

| | | | |
|---|---|---|---|
| 8,906,945 | B2 | 12/2014 | Moir et al. |
| 8,980,603 | B2 | 3/2015 | Tannous et al. |

OTHER PUBLICATIONS

Moraes et al., Current Opinion in Structural Biology (2008), 18, pp. 258-266.*
Coburn et al., Clinical Microbiology Reviews (2007), 20(4), pp. 535-549.*
Kimura et al., The Journal of Antibiotics (1996), 49(7), pp. 697-699.*
Yen et al.; NIeC, a type III secretion protease, compromises NF-kappaB activation by targeting p65/RelA. Plos Pathog, Dec. 16, 2010, vol. 6 No. 12, pp. e1001231 1-13. Especially p. 3 col. 2 para 1, p. 4 col. 1 para 1, p. 11 col. 2 para 2; Supplementary Table S1.
Tago et al.; KappaB-Ras is a nuclear-cytoplasmic small GTPase that inhibits NF-kappaB activation through the suppression of transcriptional activation of p65/RelA. J Biol Chem 1, Oct. 2010, vol. 285 No. 40 pp. 30622-30633. Especially p. 30623 col. 2 para 3.
Auerbach et al.; Innate immune recognition of Yersinia pseudotuberculosis type III secretion. PLosPathog, Dec. 2009, vol. 5 No. 12 pp. e100686 1-16. Especially p. 3 table 1, p. 4 col. 1 para 4.
Bliska et al.; Modulation of innate immune responses by Yersinia type III secretion system translocators and effectors. Cell Microbiol ePub 29, Jul. 2013, vol. 15 No. 10 pp. 1622-1631. Especially entire article [review].
International Search Report, PCT/US2014/067006, dated Apr. 8, 2015.

* cited by examiner

*Primary Examiner* — Brian J Davis
(74) *Attorney, Agent, or Firm* — Womble Bond Dickinson (US) LLP

(57) ABSTRACT

Described herein are assays for identifying piericidins and piericidin compositions.

5 Claims, 13 Drawing Sheets

A

B

Piericidin A1

Mer-A 2026B

PIERICIDIN BACTERIAL INHIBITORS

TECHNICAL FIELD

Described herein are assays for identifying inhibitors of bacterial type III secretion systems.

BACKGROUND

The bacterial type III secretion system (T3SS) is a complex multi-protein apparatus that facilitates the secretion and translocation of effector proteins from the bacterial cytoplasm directly into the mammalian cytosol. This complex protein delivery device is shared by dozens of Gram-negative pathogens, including *Salmonella* spp., *Shigella flexneri, Pseudomonas aeruginosa, Yersinia* spp., enteropathogenic and enteroinvasive *Escherichia coli*, and *Chlamydia* spp. These pathogens collectively cause over 200 million cases of human illness and greater than half a million deaths worldwide each year. They are the causative agents of plague, pneumonia, typhoid fever, and other diseases that impact human health. See, e.g., www.who.int; Morris and Potter, Eds., *Foodborne Infections and Intoxications*, Academic Press, New York, $4^{th}$ ed. (2013); Cornelius, *Nat. Rev. Microbiol.* 4: 811-825 (2006). The issue of antibiotic resistance is most pressing for Gram-negative bacteria, for which only one new class of antibiotics has been approved in the last 15 years. Projan et al., *Curr. Opin. Microbiol.* 10: 441-446 (2007); Boucher et al., *Clin. Infect. Dis.* 56: 1685-1694 (2013).

The T3SS is composed of a basal structure spanning the inner and outer bacterial membranes and a needle that extends from the bacterial surface. Moraes et al., *Curr. Opin. Struct. Biol.* 18: 258-266 (2008). This structure acts as a molecular syringe that injects bacterial effector proteins directly inside target host cells. While the structure of the T3SS is relatively conserved among T3SS-expressing bacteria, the suite of T3SS effector proteins expressed by each group of pathogens is completely distinct. Cornelius, *Nat. Rev. Microbiol.* 4: 811-825 (2006). The *Yersinia pseudotuberculosis* T3SS has been extensively studied and is often used as a model for T3SS-expressing pathogens. Duncan et al., *Antimicrob. Agents Chemother.* 56: 5433-5441 (2014), which is hereby incorporated by reference in its entirety. In *Yersinia*, the T3SS translocon proteins, LcrV, YopB, and YopD, form a pore in the mammalian plasma membrane upon host cell contact, and enable translocation of effector proteins inside the host cell cytosol. Bleves et al., *Microbes Infect.* 2: 1451-1460 (2000). *Y. pseudotuberculosis* effector proteins YopH, YopO, YopT, and YopE block phagocytosis and the formation of reactive oxygen species, while YopJ, YopM, and YopK dampen innate immune signaling. Bliska et al., *Cell Microbiol.* (2013); Clatworthy et al., *Nat. Chem. Biol.* 3: 541-548 (2007).

Although the bacterial T3SS is a broadly distributed apparatus important for disease causation, the precise mechanism of type III secretion remains incompletely understood. Thus, there remains a need to develop screening methods for identifying potent inhibitors of T3SSs in various bacterial species, including *Yersinia pseudotuberculosis.*

SUMMARY

One embodiment described herein is a method for detecting a bacterial type III secretion system inhibitor comprising: (a) providing mammalian cells with an NF-κB reporter plasmid; (b) infecting the cells with Gram-negative bacteria; (c) adding screening compounds; (d) measuring the reporter expression; and (e) identifying a compound of interest. In one aspect, the cells are HEK293T cells. In another aspect, the plasmid contains an NF-κB binding site upstream of a luciferase gene. In a further aspect, measuring reporter expression comprises measuring bioluminescence, fluorescence, absorbance, ELISA, or chemiluminescence. In a further aspect, the NF-κB site comprises the nucleotide sequence of $(GGAAAGTCCCCAGC)_5$ (SEQ ID NO:1). In another aspect, the Gram-negative bacteria are a *Yersinia pseudotuberculosis* IP2666 strain background, which naturally lacks a full-length yopT gene. One specific *Yersinia pseudotuberculosis* strain comprises mutations ablating expression of five other T3SS effector proteins (referred to as Δyop6) and another *Yersinia pseudotuberculosis* strain comprises both mutations for ablating expression of the five other T3SS effector proteins and ablating expression of a T3SS translocon component (referred to as Δyop6/ΔyopB). In one aspect, the compounds are selected and prescreened from a chemical library. In another aspect, the chemical library includes compounds generated from environmental sediment-derived marine microorganisms. In another aspect, the chemical library includes compounds generated from the class Actinomycetales, known for their prolific production of pharmacologically relevant secondary metabolites. In one aspect, the multiplicity of infection (MOI) is about 7.

Another embodiment described herein is a method for treating, prophylaxis of, or ameliorating the symptoms of, a subject infected with Gram-negative bacteria comprising administering an effective amount of a bacterial type III secretion system inhibitor.

In one aspect, the bacterial type III secretion system inhibitor comprises Piericidin A1 having a chemical formula of $C_{25}H_{37}NO_4$ and a chemical structure of (herein referred to as "Structure 1"):

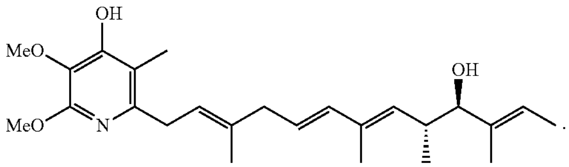 [SMILES: C/C=C(\C)[C@H](O)[C@H](C)/C=C(C)/C=C/C/C(C)=C/Cc1nc(OC)c(OC)c(O)c1C]

In another aspect, the bacterial type III secretion system inhibitor comprises a piericidin derivative, Mer-A 2026B, having a chemical formula of $C_{24}H_{35}NO_3$ and a chemical structure of (herein referred to as "Structure 2"):

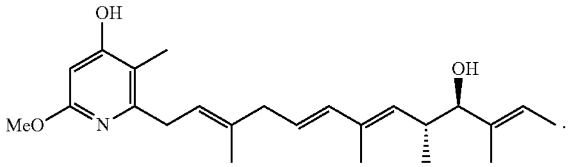 [SMILES: C/C=C(\C)[C@H](O)[C@H](C)/C=C(C)/C=C/C/C(C)=C/Cc1nc(OC)cc(O)c1C]

In another aspect, the Gram-negative bacteria are from genera comprising any one of *Chlamydia, Pseudomonas, Envinia, Pantoea, Vibrio, Burkholderia, Ralstonia, Xanthomonas, Salmonella, Shigella, Chromobacterium, Yersinia, Sodalis, Escherichia, Escherichia, Citrobacter, Edwardsiella, Mesorhizobium, Rhizobium, Aeromonas, Photorhabdus, Vibrio, Bordetella*, or *Desulfovibrio.*

In a further aspect, the Gram-negative bacteria comprise any one of *Chlamydia trachomatis, Chlamydia pneumoniae, Pseudomonas syringae, Envinia amylovora, Pantoea agglomerans, Vibrio parahaemolyticus, Burkholderia pseudomallei, Ralstonia solanacearum, Xanthomonas campestris, Salmonella enterica, Shigella flexneri, Burkholderia pseudomallei, Chromobacterium violaceum, Yersinia enterocolitica, Sodalis glossinidius, Escherichia coli, Salmonella enterica, Citrobacter rodentium, Chromobacterium violaceum, Yersinia pestis, Yersinia pseudotuberculosis, Edwardsiella tarda, Mesorhizobium loti, Rhizobium* sp., *Yersinia pseudotuberculosis, Yersinia enterocolitica, Pseudomonas aeruginosa, Aeromonas salmonicida, Photorhabdus luminescens, Vibrio parahaemolyticus, Bordetella pertussis*, or *Desulfovibrio vulgaris.*

In one aspect, the bacterial type III secretion system inhibitor is nontoxic to mammals at a dosage of about 1.0 mg/kg to about 5 mg/kg, including each integer within the specified range, assuming a mouse weighing approximately 20 g and having a blood volume of approximately 1.2 mL. In another aspect, the inhibitor is nontoxic to mammals at a dosage of about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, or about 5.0 mg/kg. In one aspect, the inhibitor is nontoxic to mammals at a dosage of about 1.75 mg/kg.

In another aspect, the bacterial type III secretion system inhibitor is nontoxic to mammals at a concentration of about 20 μM to about 200 μM, including each integer within the specified range. In another aspect, the inhibitor is nontoxic to mammals at a concentration of about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 105 μM, about 110 μM, about 115 μM, about 120 μM, about 125 μM, about 130 μM, about 135 μM, about 140 μM, about 145 μM, about 150 μM, about 155 μM, about 160 μM, about 165 μM, about 170 μM, about 175 μM, about 180 μM, about 185 μM, about 190 μM, about 195 μM, or about 200 μM. In one aspect, the inhibitor is nontoxic to mammals at a concentration of about 70 μM.

In another aspect, the bacterial type III secretion system inhibitor attenuates or inhibits the secretion of Yop effector proteins. In a further aspect, the percent inhibition of T3SS-mediated effector secretion by Piericidin A1 is about 20% to about 95%. In another aspect, the percent inhibition of T3SS-mediated effector secretion achieved by about 70 μM Piericidin A1 is about 20% to about 70% when Δyop6 in vitro effector protein secretion is monitored as an indicator of T3SS activity. In one aspect, the percent inhibition of T3SS-mediated effector secretion achieved by about 70 μM Piericidin A1 is about 20%, about 25%, about 30%, about 35%, about 40%, about 45%, about 50%, about 55%, about 60%, or about 65%, about 70%, or about 75% when Δyop6 in vitro effector protein secretion is monitored as an indicator of T3SS activity. In another aspect, the percent inhibition of T3SS-mediated effector secretion achieved by about 70 μM Piericidin A1 is about 65% when Δyop6 in vitro effector protein secretion is monitored as an indicator of T3SS activity.

In a further aspect, the percent inhibition of T3SS-mediated effector secretion by Mer-A 2026B is about 30% to about 70%. In another aspect, the percent inhibition of T3SS-mediated effector secretion achieved by about 70 μM Mer-A 2026B is about 30% to about 55% when Δyop6 in vitro effector protein secretion is monitored as an indicator of T3SS activity. In one aspect, the percent inhibition of T3SS-mediated effector secretion achieved by about 70 μM Mer-A 2026B is about 30%, about 35%, about 40%, about 45%, about 50%, or about 55% when Δyop6 in vitro effector protein secretion is monitored as an indicator of T3SS activity. In yet another aspect, the percent inhibition of T3SS-mediated effector secretion achieved by about 70 μM Mer-A 2026B is about 45% when Δyop6 in vitro effector protein secretion is monitored as an indicator of T3SS activity.

Another embodiment described herein, is a method for attenuating the growth or killing Gram-negative bacteria comprising administering an effective amount of a bacterial type III secretion system inhibitor.

In one aspect, the bacterial type III secretion system inhibitor comprises a Piericidin A1 having a chemical formula of $C_{25}H_{37}NO_4$ and the chemical structure of Structure 1.

In another aspect, the bacterial type III secretion system inhibitor comprises Mer-A 2026B having a chemical formula of $C_{24}H_{35}NO_3$ and the chemical structure of Structure 2.

In another aspect, the Gram-negative bacteria are from genera comprising any one of *Chlamydia, Pseudomonas, Envinia, Pantoea, Vibrio, Burkholderia, Ralstonia, Xanthomonas, Salmonella, Shigella, Chromobacterium, Yersinia, Sodalis, Escherichia, Escherichia, Citrobacter, Edwardsiella, Mesorhizobium, Rhizobium, Aeromonas, Photorhabdus, Vibrio, Bordetella*, or *Desulfovibrio.*

In a further aspect, the Gram-negative bacteria comprise any one of *Chlamydia trachomatis, Chlamydia pneumoniae, Pseudomonas syringae, Envinia amylovora, Pantoea agglomerans, Vibrio parahaemolyticus, Burkholderia pseudomallei, Ralstonia solanacearum, Xanthomonas campestris, Salmonella enterica, Shigella flexneri, Burkholderia pseudomallei, Chromobacterium violaceum, Yersinia enterocolitica, Sodalis glossinidius, Escherichia coli, Salmonella enterica, Citrobacter rodentium, Chromobacterium violaceum, Yersinia pestis, Yersinia pseudotuberculosis, Edwardsiella tarda, Mesorhizobium loti, Rhizobium* sp., *Yersinia pseudotuberculosis, Yersinia enterocolitica, Pseudomonas aeruginosa, Aeromonas salmonicida, Photorhabdus luminescens, Vibrio parahaemolyticus, Bordetella pertussis*, or *Desulfovibrio vulgaris.*

In one aspect, the bacterial type III secretion system inhibitor is nontoxic to mammals at a dosage of about 1.0 mg/kg to about 5 mg/kg, including each integer within the specified range, assuming a mouse weighing approximately 20 g and having a blood volume of approximately 1.2 mL. In another aspect, the inhibitor is nontoxic to mammals at a dosage of about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, or about 5.0 mg/kg. In a further aspect, the inhibitor is nontoxic to mammals at a dosage of about 1.75 mg/kg.

In another aspect, the bacterial type III secretion system inhibitor is nontoxic to mammals at a concentration of about 20 μM to about 200 μM, including each integer within the specified range. In another aspect, the inhibitor is nontoxic to mammals at a dosage of about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 105 μM, about 110 μM, about 115 μM, about 120 μM, about 125 μM, about 130 μM, about 135 μM, about 140 μM, about 145 μM, about 150 μM, about 155 μM, about 160 μM, about 165 μM, about 170 μM, about 175 μM, about 180 μM, about 185 μM, about 190 μM, about 195 μM, or about 200 μM. In a further aspect, the inhibitor is nontoxic to mammals at a concentration of about 70 μM.

In another aspect, the bacterial type III secretion system inhibitor attenuates or inhibits the secretion of Yop effector proteins. In a further aspect, the percent inhibition of T3SS-mediated effector secretion achieved by Piericidin A1 is about 20% to about 95%, including each integer within the range. In another aspect, the percent inhibition of T3SS-mediated effector secretion achieved by about 70 μM Piericidin A1 is about 20% to about 70% when Δyop6 in vitro effector protein secretion is monitored as an indicator of T3SS activity. In one aspect, the percent inhibition of T3SS-mediated effector secretion achieved by about 70 μM Piericidin A1 is about 20%, about 25%, about 30%, about 35%, about 40%, about 45%, about 50%, about 55%, about 60%, about 65%, about 70%, or about 75% when Δyop6 in vitro effector protein secretion is monitored as an indicator of T3SS activity. In one aspect, the percent inhibition of T3SS-mediated effector secretion achieved by about 70 μM Piericidin A1 is about 65% when Δyop6 in vitro effector protein secretion is monitored as an indicator of T3SS activity.

In a further aspect, the percent inhibition of T3 S S-mediated effector secretion achieved by about 70 μM Mer-A 2026B is about 30% to about 70%, including each integer within the range. In another aspect, the percent inhibition of T3SS-mediated effector secretion achieved by about 70 μM Mer-A 2026B is about 30% to about 55% when Δyop6 in vitro effector protein secretion is monitored as an indicator of T3SS activity. In one aspect, the percent inhibition of T3SS-mediated effector secretion achieved by about 70 μM Mer-A 2026B is about 30%, about 35%, about 40%, about 45%, about 50%, or about 55% when Δyop6 in vitro effector protein secretion is monitored as an indicator of T3SS activity. In one aspect, the percent inhibition of T3SS-mediated effector secretion achieved by about 70 μM Mer-A 2026B is about 45% when Δyop6 in vitro effector protein secretion is monitored as an indicator of T3SS activity.

Another embodiment described herein is a composition comprising a piericidin for attenuating the growth of or killing Gram-negative bacteria. A further embodiment described herein is a composition comprising a piericidin for treating, prophylaxis of, or ameliorating the symptoms of a Gram-negative bacterial infection. Yet another embodiment described herein is a composition comprising a piericidin used to attenuate or inhibit Gram-negative bacterial protein secretion. In one aspect, the composition is Piericidin A1 having a chemical formula of $C_{25}H_{37}NO_4$. In another aspect, the composition is Mer-A 2026B having a chemical formula of $C_{24}H_{35}NO_3$. In another aspect, the Piericidin A1 attenuates or inhibits T355-mediated effector secretion by about 65%. In a further aspect, the Mer-A 2026B attenuates or inhibits T3SS-mediated effector secretion by about 45%. In one aspect, the piericidin composition attenuates or inhibits secretion of bacterial proteins. In another aspect, the piericidin composition is used to attenuate growth or inhibit secretion of Yop effector proteins. In a further aspect, the piericidin composition is used to attenuate or inhibit growth of Gram-negative bacteria. In yet another aspect, the piericidin composition is used to attenuate or inhibit Gram-negative bacterial protein secretion. In another aspect, the piericidin composition is used for the treatment, prophylaxis of, or ameliorating the symptoms of a Gram-negative bacterial infection.

DETAILED DESCRIPTION

Figure 1:
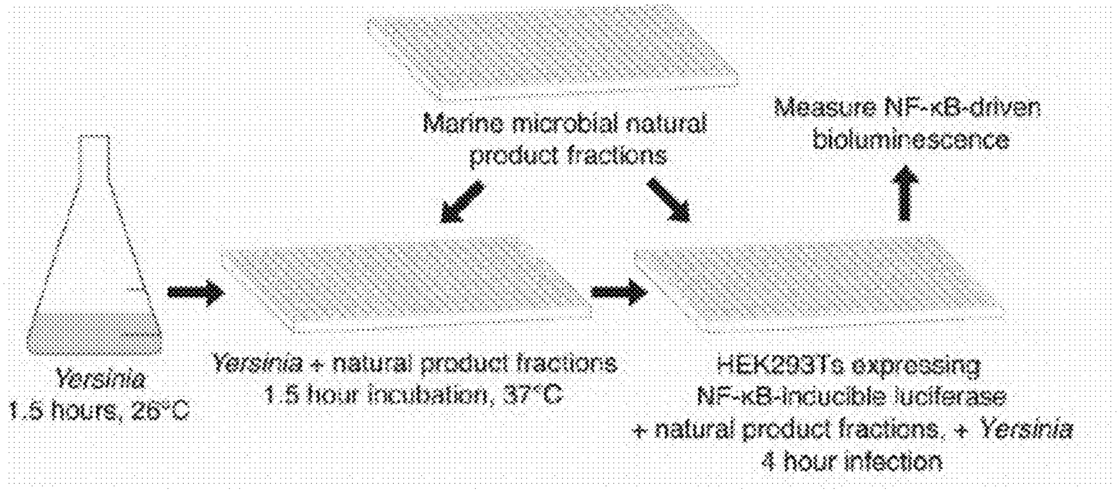
FIG. 1. NF-κB-based HTS to identify small molecule inhibitors of the *Yersinia* T3SS. *Y. pseudotuberculosis* Δyop6 was added to a 384-well plate containing compound fractions or DMSO and incubated for 1.5 hours in low calcium media at 37° C. to induce formation of the T3SS. The same compounds were robotically added to a 384-well plate containing HEK293T cells expressing an NF-κB-inducible luciferase reporter gene. The induced *Y. pseudotuberculosis* cultures were used to infect the HEK293T reporter cells at an MOI of 7. Four hours later, NF-κB driven bioluminescence was measured and served as an indicator of T3SS function in the presence of compounds.
Figure 2:
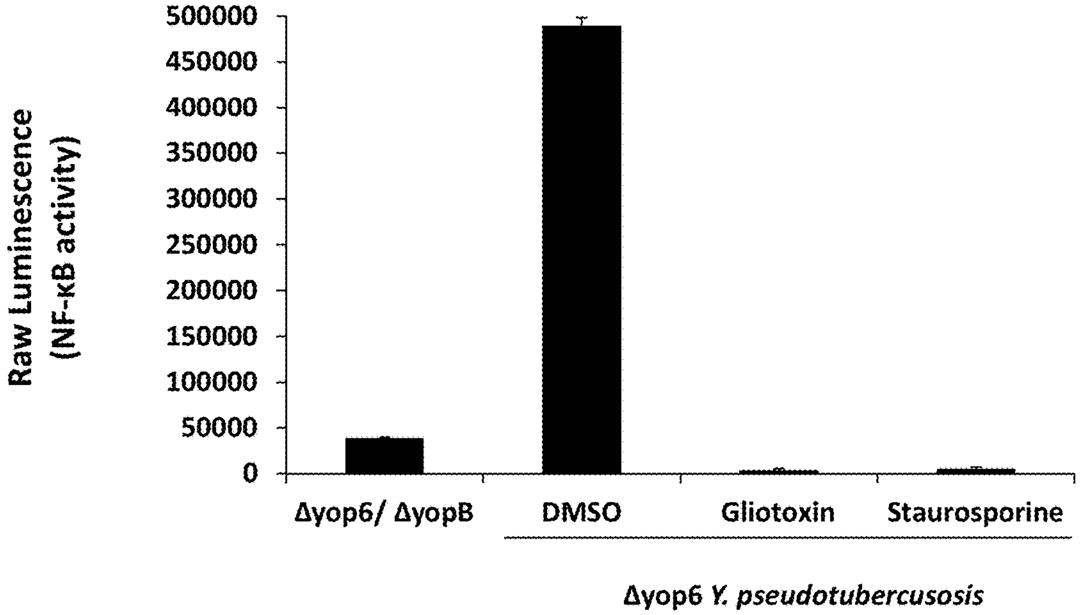
FIG. 2. Identification of compound fractions that inhibit T3SS-driven NF-κB activation, but are not toxic to mammalian cells. HEK293T cells expressing an NF-κB-inducible luciferase reporter gene were infected with *Y. pseudotuberculosis* Δyop6/ΔyopB (non-functional T3SS) or Δyop6 (functional T3SS) in the presence or absence of the cytotoxins gliotoxin and staurosporine. The average ±standard error of the mean (SEM) are shown from two independent experiments. Student t-test: *, $p<0.05$; **, $p<0.005$ relative to HEK293T cells infected with Δyop6 and DMSO-treated.

Described herein are methods for detecting bacterial type III secretion system inhibitors. Further described herein are methods and compositions for treating, prophylaxis of, or ameliorating the symptoms of bacterial infection(s) or for attenuating the growth of or killing of bacteria.

As used herein, the term "chemical library" refers to a collection of chemicals including but not limited to synthetic and natural products.

As used herein, the term "pre-fractions" refers to the separation of dried crude extracts of large-scale cultures of isolates generated from the chemical library, wherein each pre-fraction contains various amounts of small molecules.

As used herein, the term "prescreened" refers to the primary screening of crude pre-fractions to identify active constituents within a particular pre-fraction. Prescreening also reduced the number of compounds tested, eliminating those that displayed general cytotoxicity and general antibiotic activity.

As used herein, the term "multiplicity of infection" (MOI) refers to the ratio of bacteria to host cell targets. A low MOI allows for greater sensitivity in the identification of bioactive compounds.

As used herein, the term "treatment, prophylaxis of" and ameliorating the symptoms of refers to the prevention of or improvement of symptoms caused by bacterial infection.

One embodiment described herein is a method for detecting a bacterial type III secretion system inhibitor comprising providing cells with an NF-κB reporter plasmid, infecting the cells with a Gram-negative bacteria, adding screening compounds, measuring reporter expression and identifying a compound of interest.

Accordingly, in one aspect, the cells can be mammalian cells. Mammalian cells can include any human cell line such as the HEK293T cell line. Animal cells lines can also be used, including primate, rat, and mouse cell lines.

In a further aspect, the NF-κB binding site includes nucleotide sequences comprising the sequence of $(GGAAAGTCCCCAGC)_5$ (SEQ ID NO:1). In one aspect, the NF-κB binding site comprises the nucleotide sequence of SEQ ID NO:1.

In another aspect, the plasmid contains an NF-κB binding site upstream of a reporter gene. The reporter gene can be any gene that induces visually identifiable characteristics such as the luciferase, GFP or RFP genes. The reporter gene can also be a selectable marker gene such as the lacZ or chloramphenicol acetyltransferase gene.

In yet another aspect, the Gram-negative bacteria may be any Gram-negative bacteria encoding a T3SS, including those from genera comprising *Chlamydia, Pseudomonas, Envinia, Pantoea, Vibrio, Burkholderia, Ralstonia, Xanthomonas, Salmonella, Shigella, Chromobacterium, Yersinia, Sodalis, Escherichia, Escherichia, Citrobacter, Edwardsiella, Mesorhizobium, Rhizobium, Aeromonas, Photorhabdus, Vibrio, Bordetella*, or *Desulfovibrio*.

In a further aspect, the Gram-negative bacteria comprises any one of *Chlamydia trachomatis, Chlamydia pneumoniae, Pseudomonas syringae, Envinia amylovora, Pantoea agglomerans, Vibrio parahaemolyticus, Burkholderia pseudomallei, Ralstonia solanacearum, Xanthomonas campestris, Salmonella enterica, Shigella flexneri, Burkholderia pseudomallei, Chromobacterium violaceum, Yersinia enterocolitica, Sodalis glossinidius, Escherichia coli, Salmonella enterica, Citrobacter rodentium, Chromobacterium violaceum, Yersinia pestis, Yersinia pseudotuberculosis, Edwardsiella tarda, Mesorhizobium loti, Rhizobium* sp., *Yersinia pseudotuberculosis, Yersinia enterocolitica, Pseudomonas aeruginosa, Aeromonas salmonicida, Photorhabdus luminescens, Vibrio parahaemolyticus, Bordetella pertussis*, or *Desulfovibrio vulgaris*. In one aspect, the Gram-negative bacteria are *Yersinia pseudotuberculosis*.

In another aspect, the *Yersinia pseudotuberculosis* includes a mutation that ablates expression of T3SS effector proteins.

In a further aspect, the method includes a negative control that is a mutant *Yersinia pseudotuberculosis* that inhibits expression of T3SS effector proteins and inhibits expression of a translocon component protein. The translocon component maybe any of the proteins that comprise the pore in the plasma membrane upon host cell contact.

In yet another aspect, compounds are selected from the chemical library. Compounds may be secondary metabolite small molecules including alkaloids, glycosides, lipids, non-ribosomal peptides, phenazines, natural phenols, polyketides, terpenes, tetrapyrroles, piericidin families and others.

In another aspect, the chemical library includes compounds generated from environmental sediment-derived marine microorganisms.

In another aspect, the chemical library includes compounds generated from the class Actinomycetales, known for their prolific production of pharmacologically interesting secondary metabolites.

In another aspect, the compounds are prescreened from the chemical library such that the hit rate per compound is between about 0.1 and about 0.5%.

In a further aspect, the multiplicity of infection is below about 10 and provides greater sensitivity for identification of bioactive compounds.

In yet another aspect, identification of bioactive compounds includes detection by measuring bioluminescence, fluorescence, UV absorbance, ELISA, chemiluminescence, selecting for specific markers or any means of detection specific to the reporter gene used.

Another embodiment described herein, is a method for detecting a substance inhibiting a bacterial type III secretion secretory mechanism comprising transfecting cells with an NF-κB luciferase reporter plasmid, adding *Yersinia pseudotuberculosis* and compounds from a chemical library to the transfected cells at a multiplicity of infection of about 7.

Accordingly, in one aspect, the cells may be mammalian cells. Mammalian cells lines include any human cell line, such as HEK293T cells, or any animal cell line including primate, rat, and mouse cell lines.

In a further aspect, the NF-κB binding site comprises the nucleotide sequence $(GGAAAGTCCCCAGC)_5$, i.e., (SEQ ID NO:1).

In another aspect, the plasmid contains an NF-κB binding site upstream of a luciferase gene.

In yet another aspect, the *Yersinia pseudotuberculosis* includes mutations ablating expression of type III secretion effector proteins YopHEMOJT.

In another aspect, the *Yersinia pseudotuberculosis* includes mutations ablating both type III secretion effector proteins YopHEMOJT, and the translocon component YopB.

In a further aspect, compounds are selected from the chemical library. Compounds may be secondary metabolite small molecules including alkaloids, glycosides, lipids, non-ribosomal peptides, phenazines, natural phenols, polyketides, terpenes, tetrapyrroles, piericidin families and others.

In another aspect, the chemical library includes compounds generated from environmental sediment-derived marine microorganisms.

In another aspect, the chemical library includes compounds generated from the class Actinomycetales, known for their prolific production of pharmacologically interesting secondary metabolites.

In yet another aspect, the compounds are prescreened from the chemical library such that the hit rate per compound is approximately 0.3%.

In another aspect, the multiplicity of infection is about 7.

In a further aspect, identification of bioactive compounds includes detection by measuring bioluminescence.

Another embodiment described herein is a method for treating, prophylaxis of, or ameliorating the symptoms of, a subject infected with a Gram-negative bacteria comprising: administering an effective amount of a bacterial type III secretion system inhibitor. A further embodiment described herein is a method for attenuating the growth of, or killing, Gram-negative bacteria comprising administering an effective amount of a bacterial type III secretion system inhibitor.

Accordingly, in one aspect, the bacterial type III secretion system inhibitor comprises a small molecule secondary metabolite including Piericidin A1 or Mer-A 2026B.

In another aspect, the Piericidin A1 has a chemical formula of $C_{25}H_{37}NO_4$ and the chemical structure of Structure 1.

In a further aspect, the Mer-A 2026B has a chemical formula of $C_{24}H_{35}NO_3$ and the chemical structure of Structure 2.

In yet another aspect, the subject may be a mammal, including humans or animals.

In another aspect, the Gram-negative bacteria maybe any Gram-negative bacteria encoding a T3SS including those from genera comprising any one of *Chlamydia, Pseudomonas, Envinia, Pantoea, Vibrio, Burkholderia, Ralstonia, Xanthomonas, Salmonella, Shigella, Chromobacterium, Yersinia, Sodalis, Escherichia, Escherichia, Citrobacter, Edwardsiella, Mesorhizobium, Rhizobium, Aeromonas, Photorhabdus, Vibrio, Bordetella*, or *Desulfovibrio.*

In a further aspect, the Gram-negative bacteria comprises any one of *Chlamydia trachomatis, Chlamydia pneumoniae, Pseudomonas syringae, Envinia amylovora, Pantoea agglomerans, Vibrio parahaemolyticus, Burkholderia pseudomallei, Ralstonia solanacearum, Xanthomonas campestris, Salmonella enterica, Shigella flexneri, Burkholderia pseudomallei, Chromobacterium violaceum, Yersinia enterocolitica, Sodalis glossinidius, Escherichia coli, Salmonella enterica, Citrobacter rodentium, Chromobacterium violaceum, Yersinia pestis, Yersinia pseudotuberculosis, Edwardsiella tarda, Mesorhizobium loti, Rhizobium* sp., *Yersinia pseudotuberculosis, Yersinia enterocolitica, Pseudomonas aeruginosa, Aeromonas salmonicida, Photorhabdus luminescens, Vibrio parahaemolyticus, Bordetella pertussis*, or *Desulfovibrio vulgaris.*

In one aspect, the inhibitor is nontoxic to mammals at a dosage of about 1.0 mg/kg to about 5 mg/kg, including each integer within the specified range, assuming a mouse weighing approximately 20 g and having a blood volume of approximately 1.2 mL. In another aspect, the inhibitor is nontoxic to mammals at a dosage of about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, or about 5.0 mg/kg. In a further aspect, the inhibitor is nontoxic to mammals at a dosage of about 1.75 mg/kg.

In another aspect, the inhibitor is nontoxic to mammals at a concentration of about 20 μM to about 200 μM, including each integer within the specified range. In another aspect, the inhibitor is nontoxic to mammals at a dosage of about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 105 μM, about 110 μM, about 115 μM, about 120 μM, about 125 μM, about 130 μM, about 135 μM, about 140 μM, about 145 μM, about 150 μM, about 155 μM, about 160 μM, about 165 μM, about 170 μM, about 175 μM, about 180 μM, about 185 μM, about 190 μM, about 195 μM, or about 200 μM. In a further aspect, the inhibitor is nontoxic to mammals at a concentration of about 70 μM.

In yet another aspect, the effective amount of administered Piericidin A1 is about 20 μM to about 200 μM, including each integer within the specified range. In another aspect, the effective amount of administered Piericidin A1 is about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 105 μM, about 110 μM, about 115 μM, about 120 μM, about 125 μM, about 130 μM, about 135 μM, about 140 μM, about 145 μM, about 150 μM, about 155 μM, about 160 μM, about 165 μM, about 170 μM, about 175 μM, about 180 μM, about 185 μM, about 190 μM, about 195 μM, or about 200 μM. In a further aspect, the effective amount of administered Piericidin A1 is about 70 μM.

In another aspect, the effective amount of administered Mer-A 2026B is about 20 μM to about 200 μM, including each integer within the specified range. In another aspect, the effective amount of Mer-A 2026B is about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 105 μM, about 110 μM, about 115 μM, about 120 μM, about 125 μM, about 130 μM, about 135 μM, about 140 μM, about 145 μM, about 150 μM, about 155 μM, about 160 μM, about 165 μM, about 170 μM, about 175 μM, about 180 μM, about 185 μM, about 190 μM, about 195 μM, or about 200 μM. In a further aspect, the effective amount of administered derivative Mer-A 2026B is about 70 μM.

In another aspect, the inhibitor attenuates or inhibits the secretion of Yop effector proteins. In a further aspect, the percent inhibition of T3SS-mediated effector secretion by Piericidin A1 is about 20% to about 95%. In another aspect, the percent inhibition of T3SS-mediated effector secretion by about 70 μM Piericidin A1 is about 20% to about 70% when Δyop6 is secreted in vitro. In one aspect, the percent inhibition of T3SS-mediated effector secretion by about 70 μM Piericidin A1 is about 20%, about 25%, about 30%, about 35%, about 40%, about 45%, about 50%, about 55%, about 60%, about 65%, about 70%, or about 75% when Δyop6 in vitro effector protein secretion is monitored as an indicator of T3SS activity. In one aspect, the percent inhibition of T3SS-mediated effector secretion by about 70 μM Piericidin A1 is about 65% when Δyop6 in vitro effector protein secretion is monitored as an indicator of T3SS activity.

In a further aspect, the percent inhibition of T3SS-mediated effector secretion by Mer-A 2026B is about 30% to about 70%. In another aspect, the percent inhibition of T3SS-mediated effector secretion by about 70 μM Mer-A 2026B is about 30% to about 55% when Δyop6 is secreted in vitro. In one aspect, the percent inhibition of T3SS-mediated effector secretion by about 70 μM Mer-A 2026B is about 30%, about 35%, about 40%, about 45%, about 50%, or about 55% when Δyop6 in vitro effector protein secretion is monitored as an indicator of T3SS activity. In one aspect, the percent inhibition of T3SS-mediated effector secretion by about 70 μM, Mer-A 2026B is about 45% when Δyop6 in vitro effector protein secretion is monitored as an indicator of T3SS activity.

Another embodiment described herein, is a composition comprising a piericidin for attenuating the growth of or the killing of Gram-negative bacteria. A further embodiment described herein is a composition comprising a piericidin for treating, prophylaxis of, or ameliorating the symptoms of a Gram-negative bacterial infection. In yet another embodiment described herein, is a composition comprising a piericidin used to attenuate or inhibit Gram-negative bacterial protein secretion.

Accordingly, in one aspect, the bacterial type III secretion system inhibitor comprises a small molecule secondary metabolite. Secondary metabolites may include alkaloids, glycosides, lipids, nonribosomal peptides, phenazines, natural phenols, polyketides, terpenes, tetrapyrroles, piericidin families, inter alia.

In one aspect, the inhibitors include Piericidin A1 or piericidin derivative Mer-A 2026B.

In another aspect, Piericidin A1 has a chemical formula of $C_{25}H_{37}NO_4$ and the chemical structure of Structure 1.

In a further aspect, Mer-A 2026B has a chemical formula of $C_{24}H_{35}NO_3$ and a chemical structure of Structure 2.

In yet another aspect, the subject may be a mammal, including humans or animals.

In another aspect, the Gram-negative bacteria comprise, but are not limited to, any from the genera comprising *Chlamydia, Pseudomonas, Erwinia, Pantoea, Vibrio, Burkholderia, Ralstonia, Xanthomonas, Salmonella, Shigella, Chromobacterium, Yersinia, Sodalis, Escherichia, Escherichia, Citrobacter, Edwardsiella, Mesorhizobium, Rhizobium, Aeromonas, Photorhabdus, Vibrio, Bordetella*, and *Desulfovibrio*.

In another aspect, the inhibitor is nontoxic to mammals at a dosage of about 20 μM to about 200 μM, including each integer within the specified range. In another aspect, the inhibitor is nontoxic to mammals at a dosage of about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 105 μM, about 110 μM, about 115 μM, about 120 μM, about 125 μM, about 130 μM, about 135 μM, about 140 μM, about 145 μM, about 150 μM, about 155 μM, about 160 μM, about 165 μM, about 170 μM, about 175 μM, about 180 μM, about 185 μM, about 190 μM, about 195 μM, or about 200 μM. In a further aspect, the inhibitor is nontoxic to mammals at a dosage of about 70 μM.

In yet another aspect, the effective amount of administered Piericidin A1 is about 20 μM, to about 200 μM, including each integer within the specified range. In another aspect, the effective amount of administered Piericidin A1 is about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 105 μM, about 110 μM, about 115 μM, about 120 μM, about 125 μM, about 130 μM, about 135 μM, about 140 μM, about 145 μM, about 150 μM, about 155 μM, about 160 μM, about 165 μM, about 170 μM, about 175 μM, about 180 μM, about 185 μM, about 190 μM, about 195 μM, or about 200 μM. In a further aspect, the effective amount of administered Piericidin A1 is about 70 μM.

In another aspect, the effective amount of administered Mer-A 2026B is about 20 μM to about 200 μM, including each integer within the specified range. In another aspect, the effective amount of administered Mer-A 2026B is about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 105 μM, about 110 μM, about 115 μM, about 120 μM, about 125 μM, about 130 μM, about 135 μM, about 140 μM, about 145 μM, about 150 μM, about 155 μM, about 160 μM, about 165 μM, about 170 μM, about 175 μM, about 180 μM, about 185 μM, about 190 μM, about 195 μM, or about 200 μM. In a further aspect, the effective amount of administered Mer-A 2026B is about 70 μM.

In another aspect, the inhibitor attenuates or inhibits the secretion of Yop effector proteins. In a further aspect, the percent inhibition of T3SS-mediated effector secretion by Piericidin A1 is about 20% to about 95%. In another aspect, the percent inhibition of T3SS-mediated effector secretion achieved by about 70 μM Piericidin A1 is about 20% to about 70% when Δyop6 is secreted in vitro. In one aspect, the percent inhibition of T3SS-mediated effector secretion by Piericidin A1 at about 70 μM is about 20%, about 25%, about 30%, about 35%, about 40%, about 45%, about 50%, about 55%, about 60%, about 65%, about 70%, or about 75% when Δyop6 in vitro effector protein secretion is monitored as an indicator of T3SS activity. In one aspect, the percent inhibition of T3SS-mediated effector secretion achieved by about 70 μM Piericidin A1 is about 65% when Δyop6 in vitro effector protein secretion is monitored as an indicator of T3SS activity.

In a further aspect, the percent inhibition of T3SS-mediated effector secretion by Mer-A 2026B is about 30% to about 70%. In another aspect, the percent inhibition of T3SS-mediated effector secretion achieved by about 70 μM Mer-A 2026B is about 30% to about 55% when Δyop6 in vitro effector protein secretion is monitored as an indicator of T3SS activity. In one aspect, the percent inhibition of T3SS-mediated effector secretion achieved by about 70 μM Mer-A 2026B is about 30%, about 35%, about 40%, about 45%, about 50%, about 55% when Δyop6 in vitro effector protein secretion is monitored as an indicator of T3SS activity. In one aspect, the percent inhibition of T3SS-mediated effector secretion achieved by about 70 μM Mer-A 2026B is about 45% when Δyop6 in vitro effector protein secretion is monitored as an indicator of T3SS activity.

In another aspect, the compositions described herein may be used for preventing bacterial infection and growth including attenuating or inhibiting the growth of the bacteria itself and also inhibiting secretion of bacterial proteins into host target cells.

It will be readily apparent to one of ordinary skill in the relevant arts that suitable modifications and adaptations to the compositions, methods, processes, and applications described herein can be made without departing from the scope of any embodiments or aspects thereof. Having now described the various embodiments and aspects of the claimed inventions in detail, the same will be more clearly understood by reference to the following examples, which are included herewith for purposes of illustration only and are not intended to be limiting. The scope of the compositions, methods, processes, and apparati, inter alia, described herein include all actual or potential combinations of embodiments, aspects, examples, and preferences herein described. All patents and publications cited herein are incorporated by reference herein for the specific teachings thereof.

EXAMPLES

Example 1

Bacterial Growth Conditions

Bacterial strains used are listed in Table 1. *Y. pseudotuberculosis* was grown in 2×YT (yeast extract-tryptone) at 26° C. with shaking overnight. The cultures were back-diluted into low calcium media (2×YT plus 20 mM sodium oxalate and 20 mM $MgCl_2$) to an optical density ($OD_{600}$) of 0.2 and grown for 1.5 hours at 26° C. shaking followed by 1.5 hours at 37° C. to induce Yop synthesis as previously described. Auerbuch et al., *PLoS Pathog.* 5:e1000686 (2009).

TABLE 1

*Y. pseudotuberculosis* strains.

| Strain | Description | References |
|---|---|---|
| Wildtype | *Yersinia pseudotuberculosis* IP2666 (no YopT expression) | (1) |
| Δyop6 | IP2666 ΔyopHEMOJ | (2) |
| Δyop6/ΔyopB | IP2666 ΔyopHEMOJB | (2) |
| Δyop6 + pYopM-Bla | IP2666 ΔyopHEMOJ pYopM-Bla | Herein |
| Δyop6/ΔyopB + pYopM-Bla | IP2666 ΔyopHEMOJB pYopM-Bla | Herein |
| ΔyscNU | Deletion of yscNU operon | (3) |

(1) Cornelius, *Nat. Rev. Microbiol.* 4: 811-825(2006).
(2) Morris and Potter, Eds., *Foodborne Infections and Intoxications*, Academic Press, New York, 4th ed. (2013).
(3) Boucher et al., *Clin. Infect. Dis.* 56: 1685-1694 (2013).

Cell Lines

HEK293T cells were maintained in Dulbecco's modified Eagle's Medium (DMEM) supplemented with 10% Fetal Bovine Serum (FBS) and 2 mM L-glutamine at 37° C. in 5% $CO_2$. CHO-K1 cells were maintained in Ham's F-12K nutrient mixture with Kaighn's modification (F-12K) with 10% Fetal Bovine Serum (FBS) and 2 mM L glutamine at 37° C. in 5% $CO_2$.

Chemical Library and Bioassay-Guided Fractionation

A screening campaign for T3SS inhibitors was carried out using a chemical library. The library was generated by filtering organic extracts from fermented cultures and concentrating to dryness in vacuo. Dried crude extracts were pre-fractionated by solid phase extraction chromatography (5 g C18 cartridge, Supelco, USA) using a stepwise MeOH/$H_2O$ gradient: 40 mL of 10%, 20% (Fraction A), 40% (Fraction B), 60% (Fraction C), 80% (Fraction D), 100% MeOH (Fraction E) then 100% EtOAc (Fraction F). Fractions A-F were concentrated to dryness in vacuo, then resuspended in DMSO (1 mL), and aliquots of these DMSO stock solutions reformatted to 384-well plates prior to screening.

From the primary screening of crude pre-fractions, active hits were selected for peak libraries screening to identify the active constituent(s) within a particular crude pre-fraction. A 45 μL aliquot of pre-fraction DMSO stock was lyophilized and fractionated by C18 reversed-phase HPLC (Phenomenex® Synergi™ Fusion-RP, 10×250 mm column, 2 mL $min^{-1}$ flow rate) using a MeOH/$H_2O$ (0.02% formic acid) solvent system. Each pre-fraction was run on a gradient specifically tailored to produce the most highly resolved chromatography. Eluent was collected into deep well 96-well plates using an automated time-based fraction collection method consisting of 1 min time slices, and subsequently concentrated to dryness in vacuo. Dried plates were resolubilized (10 μL DMSO per well), sonicated to ensure homogeneity, reformatted to 384-well format and subjected to secondary screening.

Purified T3SS Inhibitors

Piericidin A1 and its analog Mer-A 2026B were isolated from an *Actinomycetes* strain RL09-253-HVS-A. From a large-scale culture (4 L) of the strain producing extract 1772, 0.33 g of pre-fraction D (pre-fractionation method as described above) was obtained. The active constituents were purified using C18 RP-HPLC (gradient of 58% to 88% MeOH:0.02% formic acid/$H_2O$, 2 mL/min, Synergi™ 10μ Fusion-RP column, Phenomenex®, USA, $t_R$=12.5 minutes for Mer-A 2026B and 30.5 minutes for Piericidin A1) to give 1.6 mg of Mer-A 2026B and 2.7 mg of Piericidin A1. ESITOFHRMS analysis predicted the molecular formulae $C_{24}H_{35}NO_3$ and $C_{25}H_{37}NO_4$ for Mer-A 2026B and Piericidin A1, respectively.

Mammalian Cytotoxicity

HeLa cells were incubated with microbial extracts for 19 hours and stained with Hoechst for visualizing individual nuclei. The 10% of product fractions that most reduced HeLa nuclear counts were classified as cytotoxic to mammalian cells and excluded from follow-up. This top 10% of nuclei reduction correlated strongly with the effects of previously characterized cytotoxic compounds within the training set used by Schulze et al. Schulze et al., *Chem. Biol.* 20: 285-295 (2013). For unpurified product fractions (including 1772D), the mammalian cytotoxicity data was generated by Schulze et al. Schulze et al., *Chem Biol.* 20: 285-295 (2013). The cytotoxicity data for purified Piericidin A1 and Mer-A 2026B at ≤250 μM was performed for this study.

Growth Curves

Overnight cultures of wildtype *Y. pseudotuberculosis* IP2666 were back-diluted to an optical density ($OD_{600}$) of 0.2 and 100 μL added to each well of a 96-well plate. A total of 0.3 μL of DMSO or purified compounds were added to each well. Bacteria were grown at 23° C. in 2×YT media or at 37° C. in low-calcium media (T3SS-inducing conditions) and $OD_{600}$ of the culture measured every 15 minutes for five or six hours using a VersaMax™ Tunable Microplate Reader (Molecular Devices®). The 96-well plates were continuously shaken throughout the experiment. Additional growth curves were carried out by taking samples of bacterial cultures at 0, 3, 6, and 24 hours of growth, serially diluting, and plating for colony forming units (CFUs) (FIGS. 7A-D). Starting inoculums of $4\times10^3$ or $1\times10^6$ CFU/mL were used.

The 26° C. growth curves were carried out in 500 μL of 2×YT media with continuous shaking, while the 37° C. growth curves were performed in high calcium media (2×YT plus 5 mM $CaCl_2$) to prevent induction of the T3SS and associated growth restriction. All growth curves used DMSO at 0.3%, piericidins at a concentration of ≤143 μM, or kanamycin at 50 μg/mL.

Example 2

High-Throughput Screen

On day one, 3.75×106 HEK293T cells were plated onto three 100×20 mm tissue culture dishes (BD Falcon, Franklin Lakes, N.J.) and incubated at 37° C./5% $CO_2$. On day two, the HEK293T cells were transfected with an NF-κB luciferase reporter plasmid (Stratagene, La Jolly, Calif.) using Lipofectamine 2000 (Invitrogen, Carlsbad, Calif.) according to the manufacturer's instructions. The plasmid contained an NF-κB binding site $(GGAAAGTCCCCAGC)_5$ (SEQ ID NO:1) upstream of the luciferase gene. On day three, the transfected cells were pooled and $5\times10^4$ transferred to each well of a 384-well plate. Each plate was centrifuged for 5 minutes at 290×g. *Yersinia pseudotuberculosis* overnight cultures were back-diluted into 2×YT media to an $OD_{600}$ of 0.2, and grown in a shaking incubator at 26° C. for 1.5 hours. The cultures were then pelleted by centrifugation and resuspended in half the original volume of low calcium 2×YT media. The bacteria were transferred to a 384-well plate containing low calcium media plus pre-fractions from the chemical library or plain DMSO and incubated for 1.5 hours at 37° C. Immediately prior to infection, pre-fractions or DMSO vehicle control were added to the 384-well plate containing HEK293T cells by a pinning robot. A Janus MDT pinning robot (Perkin Elmer, Waltham, Mass.) was next used to transfer *Y. pseudotuberculosis* from the bacterial 384-well plate to the HEK293T plate at a multiplicity of infection (MOI) of 7. After four hours at 37° C./5% $CO_2$, the media was aspirated before adding a 1:1 Neolite-PBS solution. Plates were covered in foil, incubated for 5 minutes, and bioluminescence measured using an EnVision plate reader (Perkin Elmer, Waltham, Mass.).

*Y. pseudotuberculosis* lacking the six known T3SS effector proteins YopHEMOJT (Δyop6) was used for this screen because YopHEMOJT are not required for T3SS dependent NF-κB induction and, instead, several Yops modulate NF-κB activation. Bliska et al., *Cell Microbiol.* (2013). A *Y. pseudotuberculosis* mutant lacking the T3SS translocon component YopB (Δyop6/ΔyopB) was used as a T3SS-negative control. *Y. pseudotuberculosis* Δyop6 in the absence of products triggered, on average, 12-fold greater luminescence than the *Y. pseudotuberculosis* Δyop6/ΔyopB mutant (data not shown).

Identification of Piericidins with T3SS Inhibitory Activity

Figure 3:
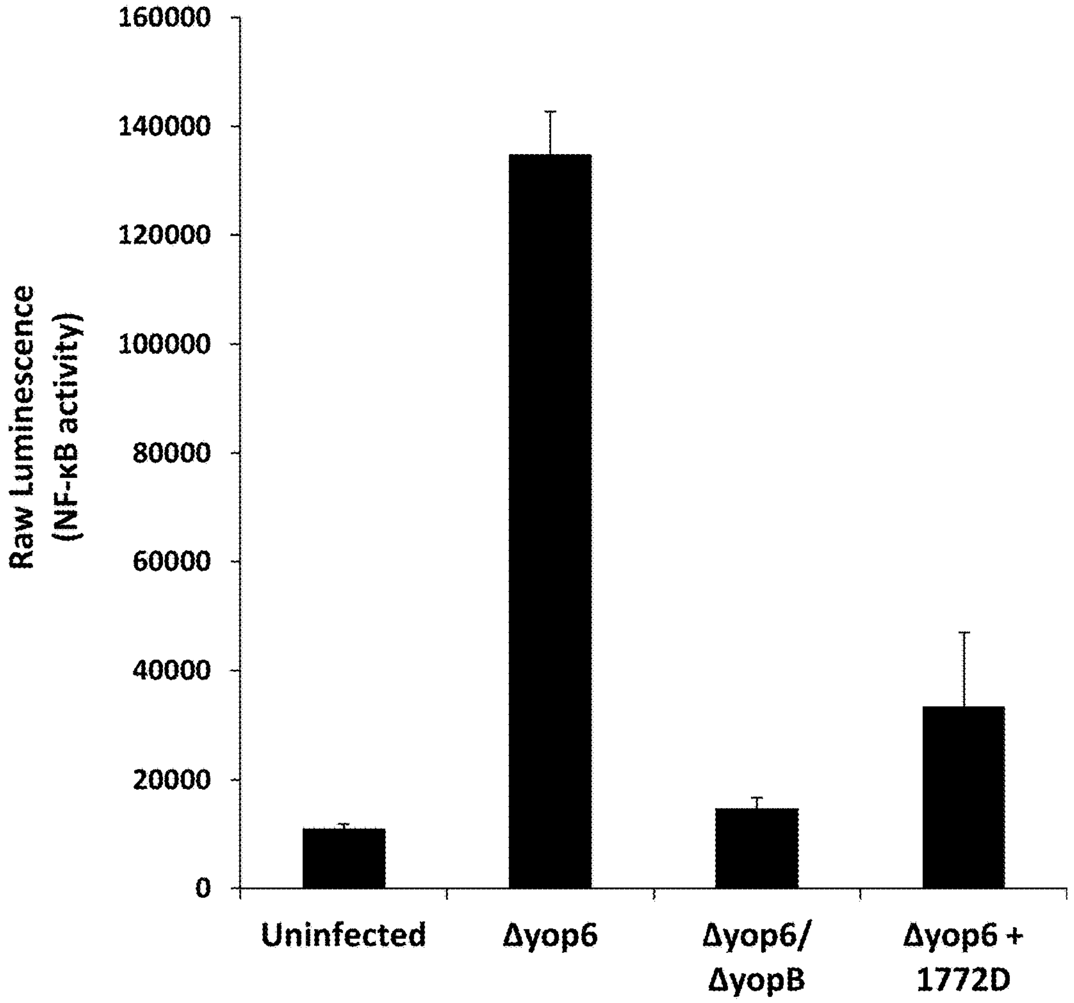
FIG. 3. Identification of compound fractions that inhibit T3SS-driven NF-κB activation, but are not toxic to mammalian cells. HEK293T cells expressing an NF-κB-inducible luciferase reporter gene were infected with *Y. pseudotuberculosis* Δyop6/ΔyopB (non-functional T3SS) or Δyop6 (functional T3SS) in the presence or absence of pre-fraction 1772D identified in our HTS. Bioluminescence was measured as an indicator of T3SS function. The average ±standard error of the mean (SEM) are shown from two independent experiments. Student t-test: *, $p<0.05$; **, $p<0.005$ relative to HEK293T cells infected with Δyop6 and DMSO-treated.
Figure 4:
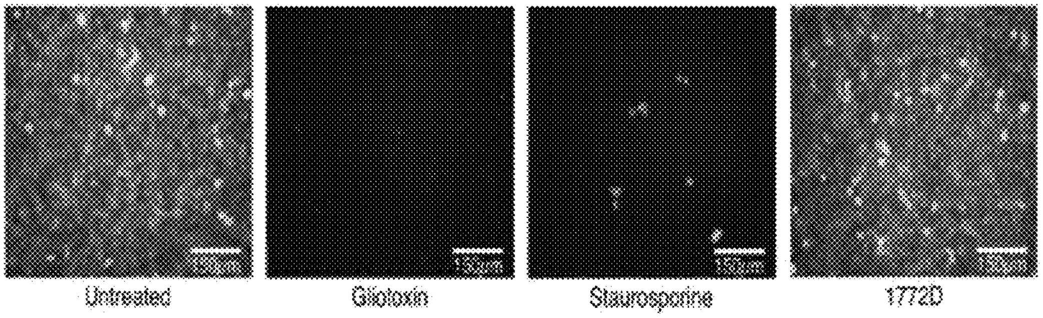
FIG. 4. HeLa cells were incubated with DMSO, staurosporine, or pre-fraction 1772D for 19 hours. Fixed cells were stained for tubulin, actin, DNA, and phosphohistone H3 (to indicate mitosis).
Figure 5:
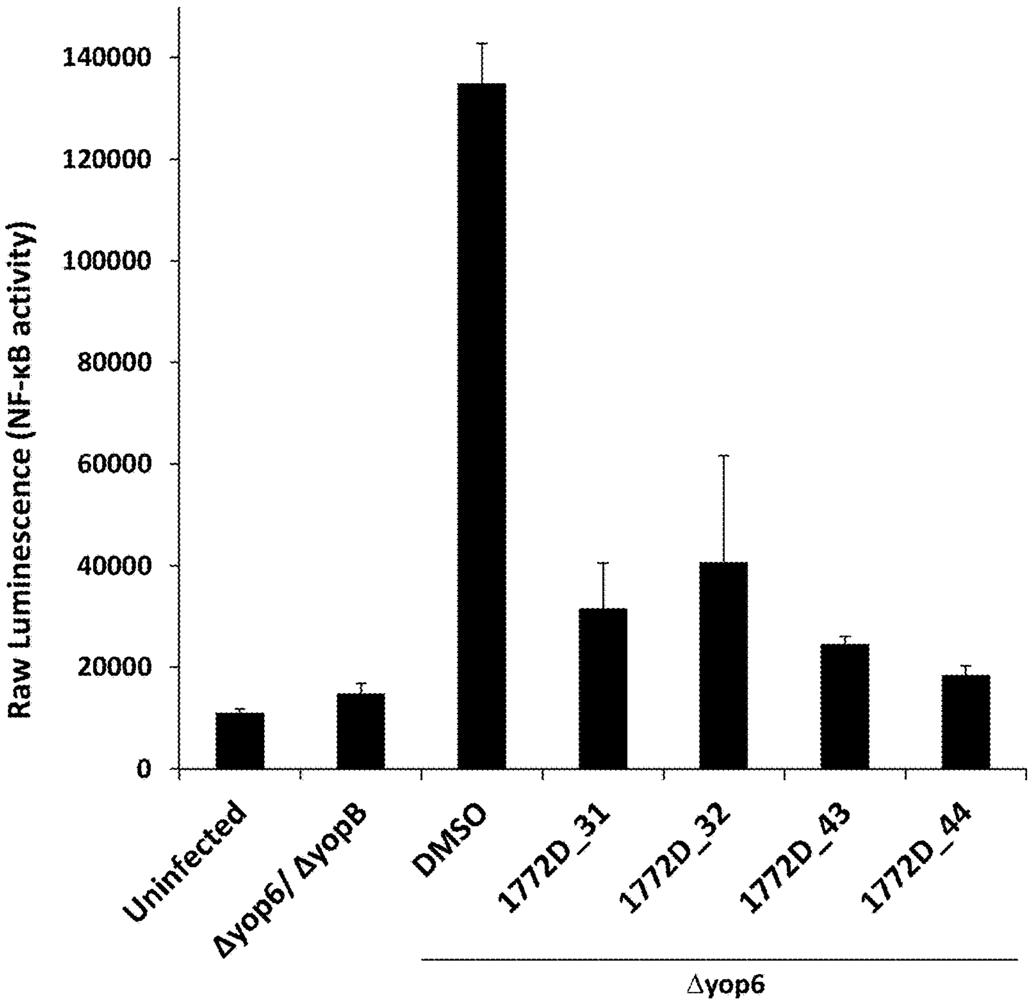
FIG. 5. Piericidin A1 and Mer-A 2026B are the bioactive constituents of pre-fraction 1772D. Pre-fraction 1772D was fractionated by HPLC630 and the eluent re-screened to identify active constituents. Fractions from minutes 31, 32, 43, and 44 contained compounds that inhibited T3SS-driven NF-κB activation in HEK293T cells. The average ±SEM are shown. Student t-test: *, $p<0.05$; **, $p<0.005$ relative to HEK293T cells infected with Δyop6 and DMSO-treated from two independent experiments.
Figure 6:
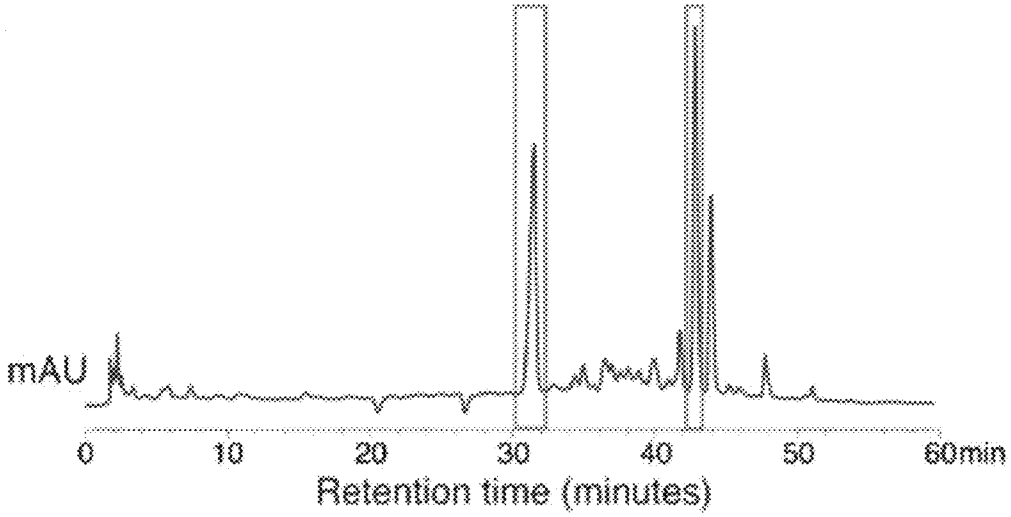
FIGS. 6A-B. Piericidin A1 and Mer-A 2026B are the bioactive constituents of pre-fraction 1772D. (A) Chromatogram (HPLC trace) of pre-fraction 1772D. Bioactive fractions 1772D_31, 32, 43 and 44 are highlighted by the boxes and contain compounds with related UV absorbance profiles. (B) Structures of Piericidin A1 and Mer-A 2026B identified through standard MS and NMR analyses.
Figure 6:
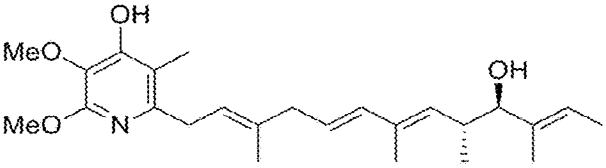
Figure 6:
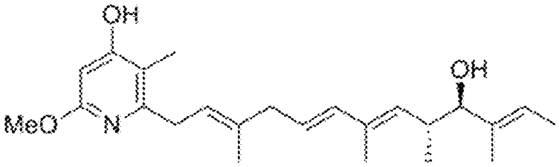

Twenty-one pre-fractions were selected for further investigation by separating the small molecules within each pre-fraction using liquid chromatography-mass spectrometry (LC-MS) to generate 'one compound-one-well' peak libraries for secondary screening. This approach provided mass spectrometric, UV absorbance and retention time data for all active constituents, and permitted direct identification of bioactive compounds from active fractions. These peak libraries were then used to repeat the experiment described above (FIG. 1) and identified individual constituents able to inhibit T3SS-driven NF-κB activation. Pre-fraction 1772D was focused on, which caused a 3.5-fold decrease in T3SS302 driven NF-κB activation (FIG. 3). In comparison to staurosporine, pre-fraction 1772D did not cause gross changes in HeLa cell morphology in the absence of bacteria (FIG. 4), indicating that the compounds in this pre-fraction were not grossly cytotoxic to mammalian cells. Upon further separation, pre-fraction 1772D yielded four fractions corresponding to 31, 32, 43, and 44 minutes of retention time on the HPLC that exhibited significant inhibition of T3SS-driven NF-κB activation (FIG. 5) and displayed tractable chromatography for compound isolation (FIG. 6A). The *Streptomyces* sp. strain RL09-253-HVS-A that produced pre-fraction 1772D and re310 ted was regrown and the bioactive compounds were purified. The structures of two related compounds found in fractions 1772D 31, 32, 43 and 44 were determined using a combination of NMR and MS experiments (FIG. 6B). The piericidin derivative Mer-A 2026B and the other as Piericidin A1 were identified.

Figure 7:
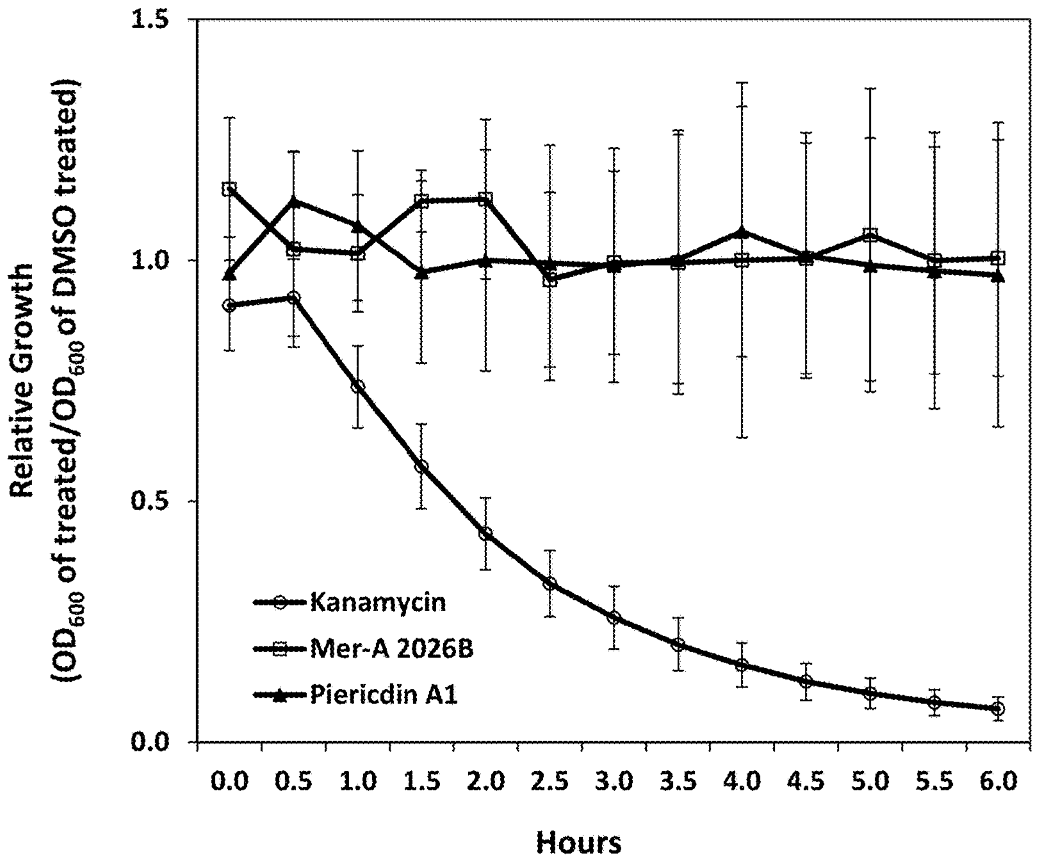
FIG. 7. Piericidin A1 and Mer-A 2026B (each at 143 μM) do not affect *Y. pseudotuberculosis* in vitro growth. Wildtype *Y. pseudotuberculosis* was grown at 23° C. with continuous shaking in the presence of DMSO, kanamycin, or piericidins. The average ±SEM of ($OD_{600}$ compound-treated)/($OD_{600}$ DMSO-treated) is shown from three independent experiments.
Figure 8:
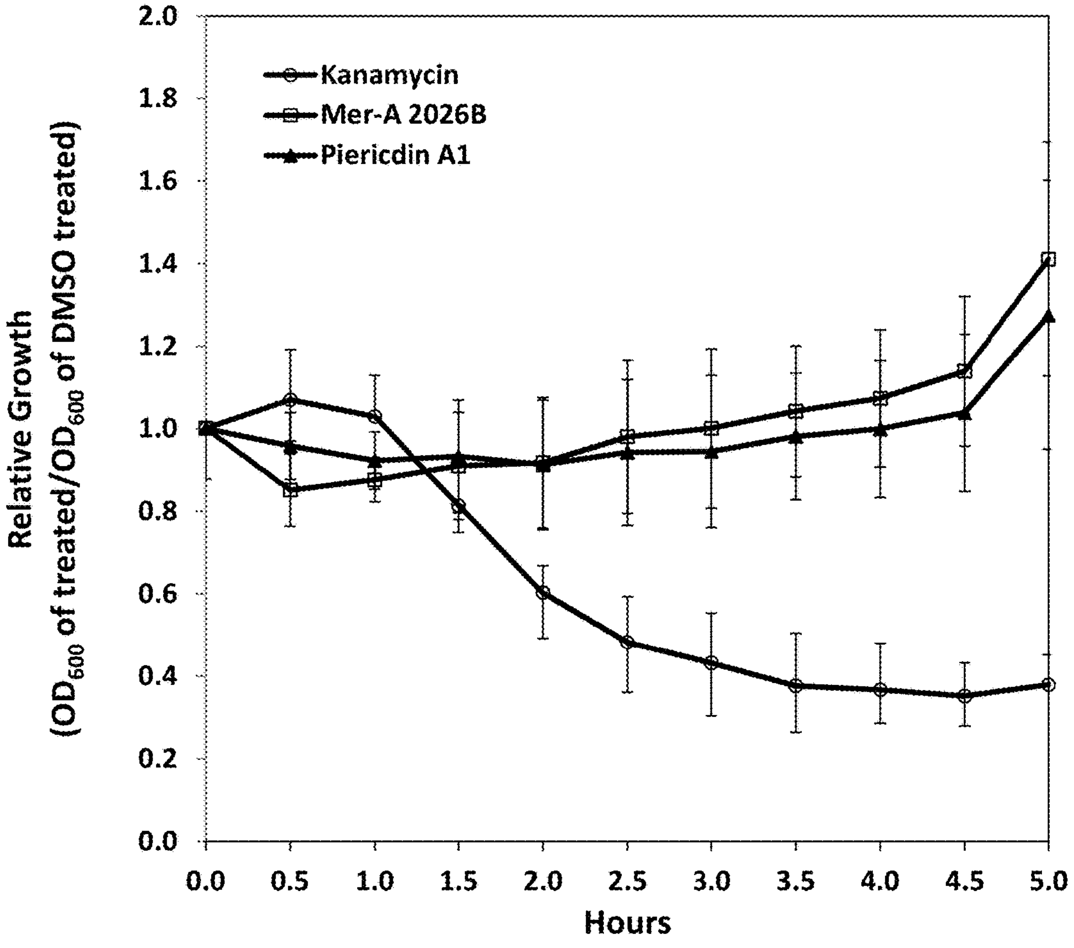
FIG. 8. Piericidin A1 and Mer-A 2026B (each at 143 μM) do not affect *Y. pseudotuberculosis* in vitro growth. Wildtype *Y. pseudotuberculosis* was grown at 37° C. with continuous shaking in the presence of DMSO, kanamycin, or piericidins. The average ±SEM of ($OD_{600}$ compound-treated)/($OD_{600}$ DMSO-treated) is shown from three independent experiments.
Figure 9:
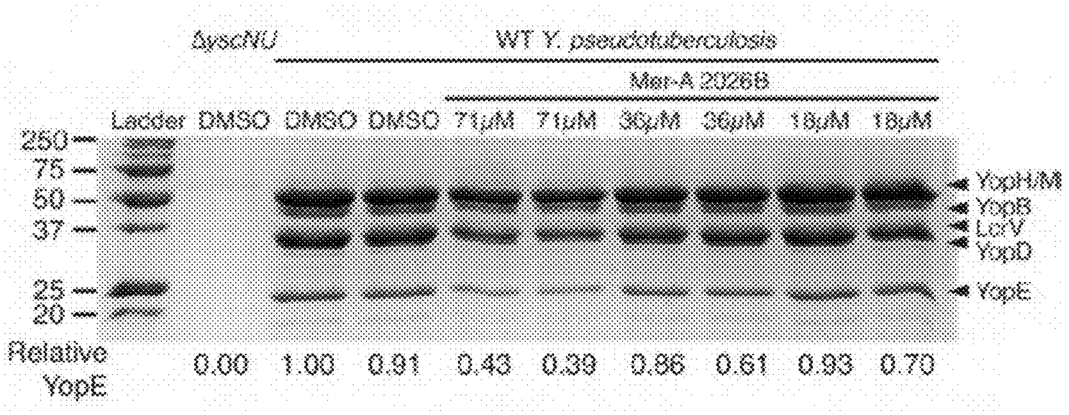
FIG. 9. Mer-A 2026B inhibits *Yersinia* type III secretion in vitro more robustly than several previously-identified T3SS inhibitors. Wildtype *Y. pseudotuberculosis* was incubated for two hours under type III secretion-inducing conditions in the presence of various concentrations of Mer-A 2026B or DMSO. The secretome was precipitated with trichloroacetic acid and analyzed by SDS-PAGE analysis. The intensity of the coomassie blue-stained band consistent with the size of YopE was quantified relative to DMSO-treated *Y. pseudotuberculosis*. Identity of the indicated YopE band was confirmed by Western blot (data not shown).

Mer-A 2026B and Piericidin A1 did not inhibit *Yersinia* growth. To confirm that the piericidins did not affect bacterial replication, growth curves of *Y. pseudotuberculosis* were performed in the presence of the purified compounds at 26° C. and 37° C. and monitored bacterial growth by optical density (FIGS. 7-8). Piericidin-treated *Y. pseudotuberculosis* grew as well or better than DMSO-treated bacteria at all tested concentrations up to 143 μM, in contrast to the known antibiotic kanamycin. More sensitive 24-hour growth curves were also performed by serially diluting and plating cultures after 0, 3, 6, and 24 hours of growth (FIGS. 7A-D). No difference was observed in bacterial replication between DMSO or 143 μM piericidin-treated *Y. pseudotuberculosis* at all time points. No colony forming units (CFUs) were recovered from kanamycin-treated cultures at 3, 6, or 24 hours of growth.

Example 3

YopM Translocation Assay

A total of $6 \times 10^3$ CHO-K1 cells were plated in each well of a 384-well plate in 70 μL of F-12K medium plus 10% FBS and incubated overnight. The following day, *Y. pseudotuberculosis* YopM-β-lactamase (YopM-Bla) reporter strain overnight cultures were back-diluted into low calcium 2×YT media to an $OD_{600}$ of 0.2, and grown in a shaking incubator at 26° C. for 1.5 hours. The cultures were then transferred to a 384-well plate containing low calcium media and purified compounds or DMSO, and incubated for 1.5 hours at 37° C. Immediately prior to infection, the purified compounds or DMSO were added to the 384-well plate containing CHO-K1 cells by a JANUS® Modular Dispense Technology™ pinning robot (Perkin Elmer®, Waltham, Mass.). The pinning robot was next used to transfer *Y. pseudotuberculosis* from the bacterial 384-well plate to the CHO-K1 plate at an MOI of 6. Five minutes following this transfer, the plate was centrifuged at 290×g for 5 minutes to initiate bacterial-host cell contact and incubated for 1 hour at 37° C./5% $CO_2$. Thirty minutes prior to the end of the infection, CCF2-AM (Invitrogen, Carlsbad, Calif.) was added to each well, and the plate was covered in foil and incubated at room temperature. At the end of the infection, the medium was aspirated and 4% paraformaldehyde was added to each well for 20 minutes to fix the cells. The paraformaldehyde was then aspirated and DRAQ5 in PBS was added to each well. The monolayers were incubated at room temperature for 10 minutes, washed once with PBS, and visualized using an ImageXpress® Micro XLS automated microscope and MetaXpress® analysis software (MolecularDevices®, Sunvale, Calif.). The number of YopM-Bla-positive cells was calculated by dividing the number of (CCF2-cleaved) cells by the number of (total CCF2+) cells. Data from three separate wells were averaged for each experiment.

Mer-A 2026B and Piericidin A1 Inhibit Translocation of YopM

To analyze the ability of the piericidins to block translocation of *Y. pseudotuberculosis* T3SS effector proteins, the translocation of a plasmid-encoded YopM-β-lactamase (YopM-Bla) reporter protein inside CHO cells was measured using the fluorescent β-lactamase substrate CCF2-AM (28). In this assay, the CHO cells were loaded with the CCF2-AM dye that normally fluoresces green. If the YopM-β-lactamase chimeric fusion is translocated into these cells, the dye is cleaved and the cells fluoresce blue, providing a quantifiable readout of T3SS-mediated translocation.

Figure 11:
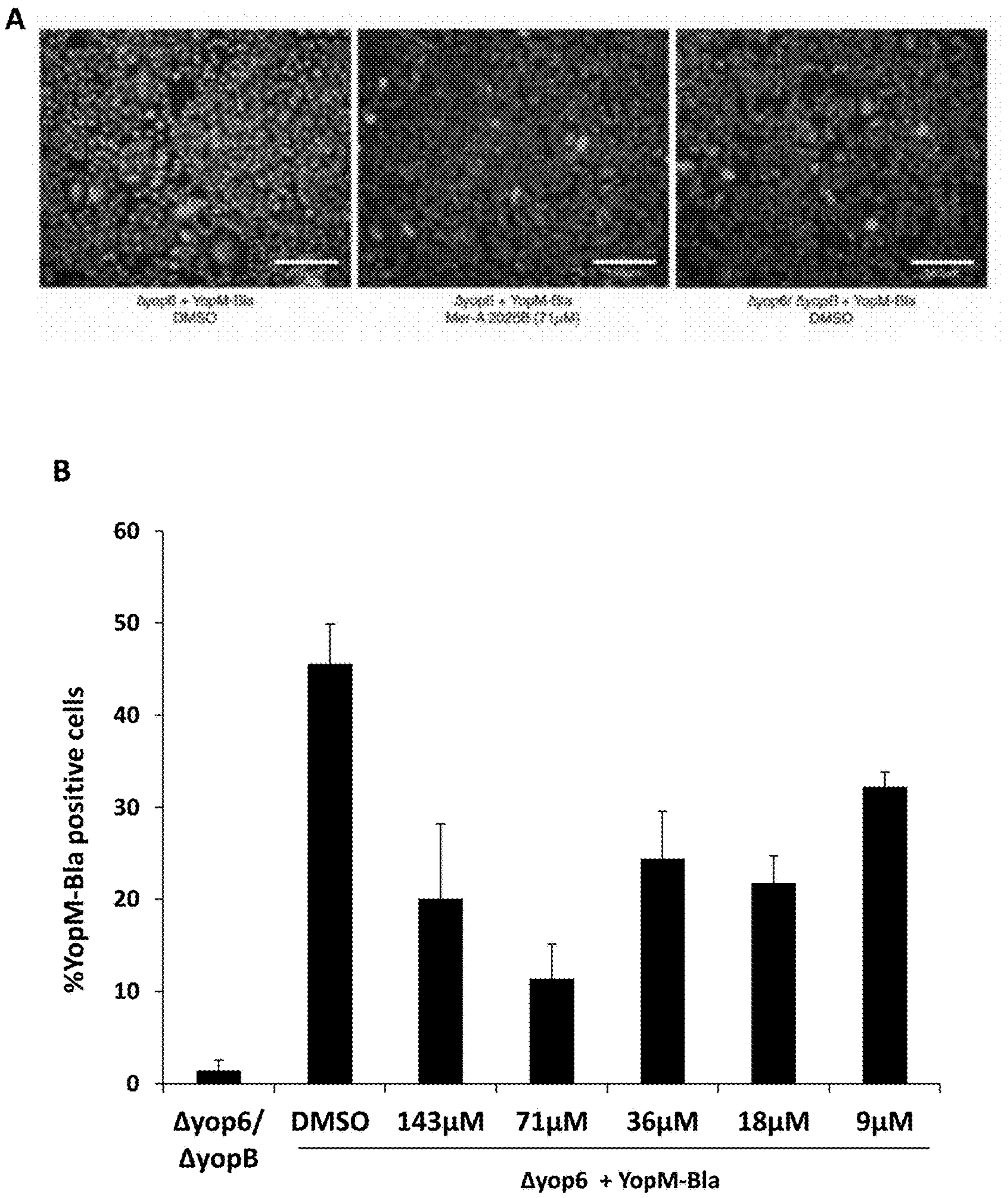
FIGS. 11A-B. Piericidin A1 and Mer-A 2026B prevent translocation of YopM-Bla into eukaryotic cells. CCF2-loaded CHO cells were infected with *Y. pseudotuberculosis* expressing a YopM-β-lactamase (Bla) reporter. The relative efficacy of YopM translocation was measured by quantifying the intensity of uncleaved CCF2 and cleaved CCF2. (A) Representative images (for Mer-A 2026B) and (B) the average percentage of cells (that were injected with YopM-Bla) out of the total cells (those that took up CCF2)±SEM from 3-4 independent experiments. Student t-test: *, $p<0.05$; **, $p<0.005$ relative to DMSO-treated.
Figure 12:
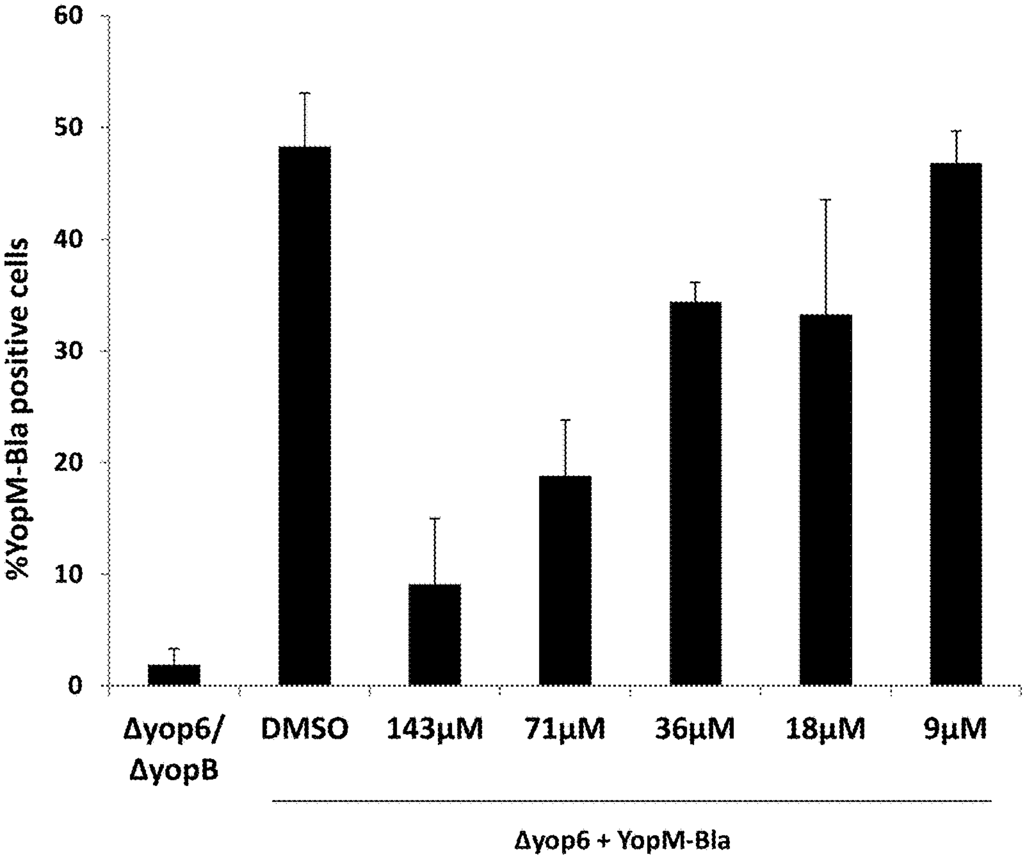
FIG. 12. For Piericidin A1, the average percentage of cells (that were injected with YopM-Bla) out of the total cells (those that took up CCF2)±SEM from 3-4 independent experiments. Student t-test: *, $p<0.05$; **, $p<0.005$ relative to DMSO-treated.
Figure 13:
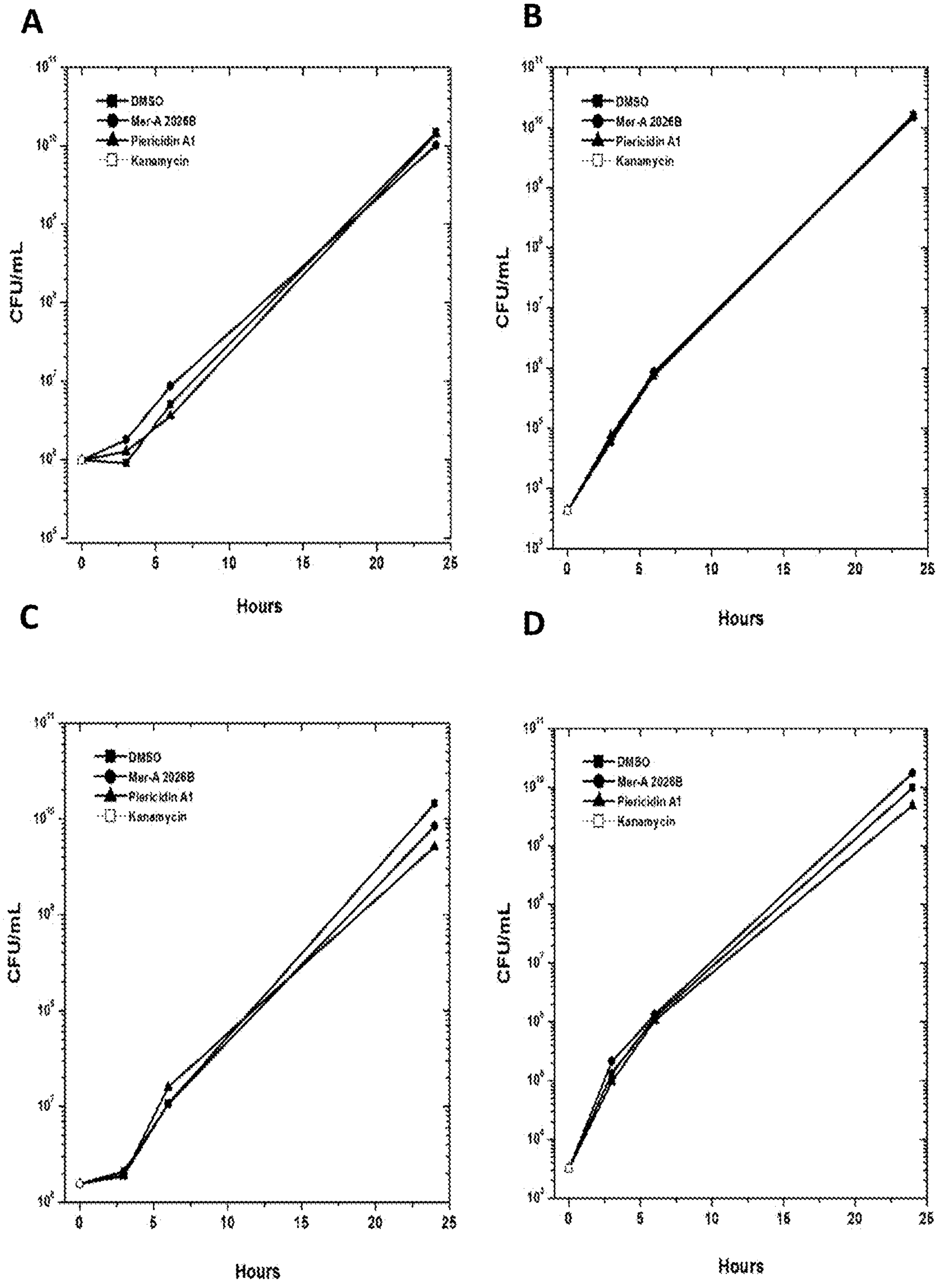
FIGS. 13A-D. Growth curves measured by serial dilution and plating for colony forming units (CFUs). Wild type *Y. pseudotuberculosis* was grown for 24 hours with continuous shaking in the presence of DMSO, piericidins (143 μM), or kanamycin. CFUs/mL were measured at 0, 3, 6, and 24 hours of growth at 26° ° C. (A and B) and 37° C. (C and D).

The Mer-A 2026B significantly reduced YopM translocation into CHO cells at all concentrations (FIG. 11B), ranging from 9 μM to 143 μM. The 71 μM concentration displayed the most robust T3SS inhibition, 75% ($p<0.05$). Piericidin A1 also significantly diminished YopM-β-lactamase translocation at concentrations of 36 μM and greater (FIG. 12). These results validate that the piericidins identified through the HTS screen inhibited T3SS effector translocation into eukaryotic cells.

Example 4

Type III Secretion Assay

Visualization of T3SS cargo secreted in broth culture was performed as previously described. Auerbuch et al., *PLos Pathog.* 5:e1000686 (2009). *Y. pseudotuberculosis* low calcium media cultures were grown for 1.5 hrs at 26° C. Purified compounds or DMSO were added and the cultures were switched to 37° C. for another 2 hrs. Cultures were spun down at 13,200 rpm for 10 min at room temperature. Supernatants were transferred to a new eppendorf tube. Ten percent final trichloroacetic acid was added and the mixture vortexed vigorously. Samples were incubated on ice for 20 minutes and then spun down at 13,200 rpm for 15 minutes at 4° C. The pellet was resuspended in final sample buffer (FSB)+20% DTT. Samples were boiled for 5 minutes prior to running on a 12.5% SDS-PAGE gel. Sample loading was normalized for bacterial density ($OD_{600}$) of each sample. Densitometric quantification of the bands was done using Image Lab software (Bio-Rad), setting the first DMSO-treated wildtype *Y. pseudotuberculosis* YopE band to 1.00.

Mer-A 2026B and Piericidin A1 Inhibits Secretion of Yops In Vitro

The ability of *Y. pseudotuberculosis* to secrete effector Yops into broth culture in the presence of the piericidins or five previously identified, commercially available T3SS inhibitors was evaluated. MBX-1641 and aurodox were shown to reduce in vitro type III secretion by *Yersinia pestis* and *Escherichia coli*, respectively, and were chosen as positive controls. In contrast, C15, C22, and C24 were shown to inhibit translocation of effector proteins inside host cells, but not Yop secretion in vitro and were chosen as negative controls. Harmon et al., *Antimicrob. Agents Chemother.* 54: 3241-3254 (2010). *Y. pseudotuberculosis* was grown in the presence of purified compounds or DMSO for 2 hours at 37° C. in the absence of calcium (T3SS-inducing conditions). Secreted proteins were precipitated from the supernatant and analyzed relative protein abundance using SDS-PAGE analysis.

Figure 10:
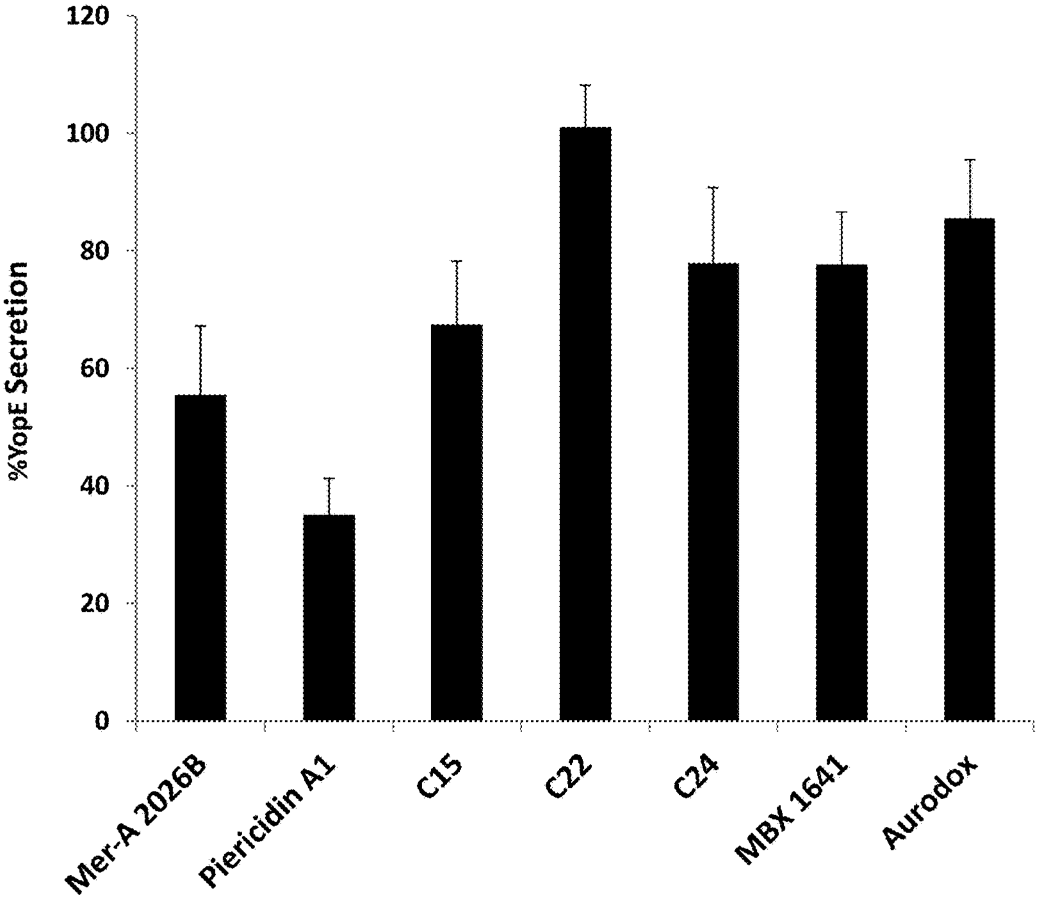
FIG. 10. The experiment in FIG. 9 was repeated using Piericidin A1 and previously identified commercially-available T3SS inhibitors C15, C22, and C24 and MBX1641 at a final concentration of 71 μM (data not shown). Harmon et al., *Antimicrob. Agents Chemother.* 54: 3241-3254 (2010); Kimura et al., *J. Antibio*. (Tokyo) 64: 197-203 (2011); and Aiello, et al., *Antimicrob. Agents Chemother.* 54: 1988-1999 (2010). Aurodox was used at a final concentration of 12.5 μM (21). Kimura et al., *J. Antibio*. (Tokyo) 64: 197-203 (2011). The average inhibition of YopE secretion by the T3SS inhibitors compared to DMSO (inhibitor-treated YopE band intensity)/(DMSO-treated YopE band intensity)±SEM from 3-4 independent experiments is shown. Student t-test: *, $p<0.05$; **, $p<0.02$ relative to DMSO-treated wild type *Y. pseudotuberculosis*.

Mer-A 2026B at a concentration of 71 μM reduced secretion of the T3SS effector YopE by 45% ($p<0.02$), while lower concentrations of inhibitor demonstrated a dose dependent decrease in inhibition (FIG. 10). Piericidin A1 blocked type III secretion by 65% (FIG. 10). MBX 1641 and C15 at a concentration of 71 μM also significantly reduced YopE secretion, although this inhibition was only 22-33% ($p<0.05$; $p<0.04$, respectively). Aiello, et al., *Antimicrob. Agents Chemother.* 54: 1988-1999 (2010); Harmon et al., *Antimicrob. Agents Chemother.* 54: 3241-3254 (2010). C22 and C24 did not significantly reduce T3S. C15, however, did block in vitro secretion. Aurodox did not significantly inhibit YopE secretion at the highest concentration used, 12.5 μM (FIG. 10). Kimura et al., *J. Antibio.* (Tokyo) 64: 197-203 (2011). Aurodox at 71 μM was not tested, as Kimura et al. found that concentrations above 12.5 μM were cytotoxic to *E. coli.*

What is claimed is:

1. A method of inhibiting bacterial type three secretion system mediated effector protein translocation from a Gram negative bacterium into a eukaryotic cell, the method comprising: administering a composition comprising Piericidin A1 or Piericidin derivative Mer-A 2026B, provided that the composition delivers a concentration of at least 18 μM Piericidin A1 or Piericidin derivative Mer-A 2062B to the Gram negative bacterium.

2. The method of claim 1, wherein the Gram-negative bacterium is from the genus *Yersinia.*

3. The method of claim 2, wherein the Gram-negative bacterium is *Yersinia pestis, Yersinia pseudotuberculosis*, or *Yersinia enterocolitica.*

4. The method of claim 1 wherein the effector protein is a Yop effector protein.

5. The method of claim 1 wherein the concentration of Piericidin A1 or Piericidin derivative Mer-A 2062B delivered to the Gram negative bacterium is at least 70 μM.

* * * * *